United States Patent [19]

Boyle et al.

[11] Patent Number: 5,032,607

[45] Date of Patent: Jul. 16, 1991

[54] USE OF OLEFINIC COMPOUNDS

[75] Inventors: Francis T. Boyle, Congleton; Zbigniew S. Matusiak, Crewe; James M. Wardleworth, Macclesfield, all of England

[73] Assignee: Imperial Chemical Industries PLC, London, England

[21] Appl. No.: 369,676

[22] Filed: Jun. 21, 1989

Related U.S. Application Data

[62] Division of Ser. No. 218,246, Jul. 13, 1988, Pat. No. 4,866,086.

[30] Foreign Application Priority Data

Jul. 15, 1987 [GB] United Kingdom ............... 8716650

[51] Int. Cl.$^5$ ..................... A61K 31/41; C07D 249/08
[52] U.S. Cl. .................................. 514/383; 548/262.2
[58] Field of Search .......................... 548/262; 514/383

[56] References Cited

U.S. PATENT DOCUMENTS

| | | | |
|---|---|---|---|
| 4,086,351 | 4/1978 | Balasubramanyan | 548/262 X |
| 4,104,399 | 8/1978 | Pommer | 548/262.2 X |
| 4,140,782 | 2/1979 | Timmler et al. | 514/383 |
| 4,495,191 | 1/1985 | Ehrhardt | 548/262.2 X |
| 4,647,302 | 3/1987 | Reiser et al. | 548/262 X |
| 4,663,338 | 5/1987 | Janssen et al. | 514/383 |
| 4,740,515 | 4/1988 | Weissmüller | 514/383 |
| 4,780,471 | 10/1988 | Maeda et al. | 548/262 X |
| 4,855,510 | 8/1989 | Noon et al. | 548/262 X |

OTHER PUBLICATIONS

Chemical Abstracts Service, CA100(7):51583h, Abstract of DE 3210570, Oct. 6, 1983, (Ehrhardt).
Chemical Abstracts Service, CA89(13):109507;, Abstract of DE 2652313, May 18, 1978, (Pommer).

*Primary Examiner*—Catherine S. Kilby Scalzo
*Attorney, Agent, or Firm*—Cushman, Darby & Cushman

[57] ABSTRACT

The use of an olefinic compound of the formula

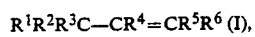

$$R^1R^2R^3C-CR^4=CR^5R^6 \quad (I),$$

wherein $R^1$ is a heterocyclyl radical selected from 1,2,4-triazolyl, imidazolyl, 5-(1-6C alkyl)imidazol-1-yl, pyridyl and pyrimidinyl; $R^2$ and $R^3$, which may be the same or different, are each a hydrogen atom or a 1-6C alkyl radical; $R^4$ is a phenyl or pyridyl radical, optionally bearing one or more substitutents selected from halogen atoms, amino, cyano, carbamoyl and nitro radicals, 1-6C alkyl, halogenoalkyl, alkoxy, halogenoalkoxy, alkylamino and alkylcarbamoyl radicals, di(1-6C alkyl)amino, di(1-6C alkyl)carbamoyl and 2-6C alkoxycarbonyl radicals; $R^5$ is a hydrogen or halogen atom, a 1-6C alkyl radical or a phenyl radical optionally bearing one or more substituents as defined above for $R^4$; and $R^6$ is a phenyl or pyridyl radical optionally bearing one or more substitutents as defined above for $R^4$; or, for those compounds which contain a basic nitrogen atom, the pharmaceutically or veterinarily acceptable salts thereof, for the manufacture of a pharmaceutical or veterinary composition having utility as an aromatase inhibitor.

2 Claims, No Drawings

USE OF OLEFINIC COMPOUNDS

This is a division of application Ser. No. 07/218,246, filed 7/13/88 now U.S. Pat. No. 4,866,086, issued on Sept. 12, 1989.

This invention relates to the use of olefinic compounds in the manufacture of pharmaceutical and veterinary compositions possessing aromatase inhibitory activity, and to certain of such olefinic compounds which are novel, and more particularly it relates to the use of such olefinic compounds, and such novel compounds per se which are styryl derivatives.

Aromatase is an enzyme which effects aromatisation of ring A in the metabolic formation of various steroid hormones. Various cancers, for example breast cancer, are dependent upon circulating steroid hormones which have an aromatic ring A. Such cancers can be treated by removing the source of ring A aromatised steroid hormones, for example by the combination of oophorectomy and adrenalectomy. An alternative way of obtaining the same effect is by administering a chemical compound which inhibits the aromatisation of the steroid ring A, and the compositions manufactured by the use of this invention, and the novel compounds of this invention are useful for this purpose.

Thus, according to the invention, there is provided the use of an olefinic compound of the formula $$R^1R^2R^3C-CR^4=CR^5R^6 \quad (I),$$

wherein $R^1$ is a heterocyclyl radical selected from 1,2,4-triazolyl, imidazolyl, 5-(1-6C alkyl)imidazol-1-yl, pyridyl and pyrimidinyl; $R^2$ and $R^3$, which may be the same or different, are each a hydrogen atom or a 1-6C alkyl radical; $R^4$ is a phenyl or pyridyl radical, optionally bearing one or more substituents selected from halogen atoms, amino, cyano, carbamoyl and nitro radicals, 1-6C alkyl, halogenoalkyl, alkoxy, halogenoalkoxy, alkylamino and alkylcarbamoyl radicals, di(1-6C alkyl)amino, di(1-6C alkyl)carbamoyl and 2-6C alkoxycarbonyl radicals; $R^5$ is a hydrogen or halogen atom, a 1-6C alkyl radical or a phenyl radical optionally bearing one or more substituents as defined above for $R^4$; and $R^6$ is a phenyl or pyridyl radical optionally bearing one or more substituents as defined above for $R^4$; or, for those compounds which contain a basic nitrogen atom, the pharmaceutically or veterinarily acceptable salts thereof, for the manufacture of a pharmaceutical or veterinary composition having utility as an aromatase inhibitor.

A suitable value for the heterocyclyl radical $R^1$ is, for example, a 1,2,4-triazol-1-yl, 1-imidazolyl, 5-methylimidazol-1-yl, 3-pyridyl or 5-pyrimidinyl radical.

A suitable value for $R^6$ when it is a pyridyl radical is, for example, a 2-pyridyl radical, and a particular such pyridyl radical is a 5-cyano-2-pyridyl radical.

A suitable value for any of $R^2$, $R^3$ or $R^5$, when any of them is a 1-6C alkyl radical, or for an optional 1-6C alkyl substituent in $R^4$, $R^5$ (when it is a substituted phenyl radical) or $R^6$ is, for example, a methyl, ethyl, propyl, isopropyl, butyl, isobutyl, sec-butyl, tert-butyl, pentyl or hexyl radical.

A suitable value for an optional halogen substituent in $R^4$, $R^5$ (when it is a substituted phenyl radical) or $R^6$ is, for example, a fluorine, chlorine or bromine atom.

A suitable value for $R^5$ when it is a halogen atom is, for example, a fluorine atom.

Suitable values for $R^4$, $R^5$ and $R^6$, when any of them is a halogen-substituted phenyl radical, are, for example, 2-, 3- and 4-fluorophenyl, 2-, 3- and 4-chlorophenyl, 2-, 3- and 4-bromophenyl, 2,3-, 2,4-, 2,5-, 2,6-, 3,4- and 3,5-difluorophenyl, 2,3-, 2,4-, 2,5-, 2,6-, 3,4- and 3,5-dichlorophenyl, and phenyl bearing mixed halogen substituents, for example 2-chloro-4-fluorophenyl or 4-chloro-2-fluorophenyl radicals.

A suitable value for a 1-6C halogenoalkyl substituent in $R^4$, $R^5$ (when it is a substituted phenyl radical) or $R^6$ is, for example, a fluoromethyl, difluoromethyl, trifluoromethyl, trichloromethyl, 1- or 2-fluoroethyl, 1,2- or 2,2-difluoroethyl, 1,1,2-, 1,2,2- or 2,2,2-trifluoroethyl, 1,1,2,2-tetrafluoroethyl, pentafluoroethyl, 1-or 2-chloroethyl, 2,2,2-trichloroethyl, 2,2,3,3,3-pentafluoropropyl, 4,4,4-trifluorobutyl, 5-chloropentyl or 6-bromohexyl radical.

A suitable value for a 1-6C alkoxy substituent in $R^4$, $R^5$ (when it is a substituted phenyl radical) or $R^6$ is, for example, a methoxy, ethoxy, propoxy, isopropoxy, butoxy, isobutoxy, sec-butoxy, tert-butoxy, pentyloxy, neopentyloxy or hexyloxy radical.

A suitable value for a 1-6C halogenoalkoxy substituent in $R^4$, $R^5$ (when it is a substituted phenyl radical) or $R^6$ is, for example, a trichloromethoxy, fluoromethoxy, trifluoromethoxy, 1,1-, 1,2- or 2,2-difluoromethoxy, pentafluoroethoxy or 2,2,3,3,3-pentafluoropropoxy radical.

A suitable value for a 1-6C alkylamino substituent in $R^4$, $R^5$ (when it is a substituted phenyl radical) or $R^6$ is, for example, a methylamino, ethylamino, propylamino, isopropylamino, butylamino, isobutylamino, sec-butylamino, tert-butylamino, pentylamino, or hexylamino radical, and a suitable value for a di(1-6C alkyl)amino substituent is, for example, a dimethylamino, ethylmethylamino, diethylamino, methylpropylamino, ethylpropylamino, dipropylamino, dibutylamino, methylhexylamino or dihexylamino radical.

A suitable value for a 1-6C alkylcarbamoyl substituent in $R^4$, $R^5$ (when it is a substituted phenyl radical) or $R^6$ is, for example, a methylcarbamoyl, ethylcarbamoyl, propylcarbamoyl, isopropylcarbamoyl, butylcarbamoyl, pentylcarbamoyl or hexylcarbamoyl radical, and a suitable value for a di(1-6C alkyl) carbamoyl substituent is, for example, a dimethylcarbamoyl, ethylmethylcarbamoyl, diethylcarbamoyl, methylpropylcarbamyl, ethylpropylcarbamoyl, dipropylcarbamoyl or hexylmethylcarbamoyl radical.

A suitable value for a 2-6C alkoxycarbonyl substituent in $R^4$, $R^5$ (when it is a substituted phenyl radical) or $R^6$ is, for example, a methoxycarbonyl, ethoxycarbonyl, propoxycarbonyl, isopropoxycarbonyl, butoxycarbonyl or pentyloxycarbonyl radical.

A suitable pharmaceutically or veterinarily acceptable salt is, for example, the hydrochloride, nitrate, sulphate, phosphate, acetate, lactate, citrate, maleate or fumarate.

The double bond in the olefinic compound of the formula I may be in the E or Z conformation, or the compound may be a mixture of the E and Z forms.

In addition, the carbon atom bearing the substituents $R^1$, $R^2$ and $R^3$ may be asymmetrically substituted, so that the compound of the formula I may exist in racemic or optically active form. It is common general knowledge in the art how such a racemate may be resolved into its stereoisomers, or how such stereoisomers may be synthesized, and their aromatase inhibitory activity determined.

A preferred group of compounds, for use in the manufacture of a pharmaceutical or veterinary composition in accordance with the invention, comprises those compounds wherein $R^4$ is a cyanophenyl group, and more particularly those compounds wherein $R^4$ is a 4-cyanophenyl radical.

A further preferred group of compounds, for use in the manufacture of a pharmaceutical or veterinary composition in accordance with the invention, comprises those compounds wherein $R^5$ is a hydrogen atom and $R^6$ is a cyanophenyl, chlorophenyl, dichlorophenyl, fluorophenyl, trifluoromethylphenyl or cyano-2-pyridyl radical, especially a 4-cyanophenyl, 4-chlorophenyl, 2,4-dichlorophenyl, 4-fluorophenyl, 4-trifluoromethylphenyl or 5-cyano-2-pyridyl radical, and particularly preferred are such compounds wherein $R^4$ has the preferred value defined above.

A further preferred group of compounds, for use in the manufacture of a pharmaceutical or veterinary composition in accordance with the invention comprises those compounds wherein $R^1$ is a 1,2,4-triazol-1-yl, imidazol-1-yl or 5-methylimidazol-1-yl and particularly preferred are such compounds wherein $R^4$, $R^5$ and $R^6$ have the preferred values defined above.

Particular preferred compounds which may be used for the manufacture of a pharmaceutical or veterinary composition in accordance with the invention are (Z)-α-(1,2,4-triazol-1-ylmethyl)stilbene-4,4'-dicarbonitrile, (Z)-4'-chloro-α-(1,2,4-triazol-1-ylmethyl)stilbene-4-carbonitrile, (Z)-α-(1,2,4-triazol-1-ylmethyl)-4'-(trifluoromethyl)stilbene-4-carbonitrile, (E)-β-fluoro-α-(1,2,4-triazol-1-ylmethyl)stilbene-4,4'-dicarbonitrile, (Z)-4'-fluoro-α-(imidazol-1-ylmethyl)stilbene-4-carbonitrile, (Z)-2', 4'-dichloro-α-(imidazol-1-ylmethyl)-stilbene-4-carbonitrile (Z)-4'-chloro-α-(imidazol-1-ylmethyl)stilbene-4-carbonitrile, (Z)-α-(imidazol-1-ylmethyl)stilbene-4,4'-dicarbonitrile, (Z)-α-(5-methylimidazol-1-ylmethyl)stilbene- 4,4'-dicarbonitrile and (Z)-2-[2-(4-cyanophenyl)-3-(1,2,4-triazol-1-yl)propenyl]pyridine-5-carbonitrile.

According to a further feature of the invention there is provided a pharmaceutical or veterinary composition comprising an olefinic compound of the formula I as defined above, together with a pharmaceutically or veterinarily acceptable diluent or carrier.

The pharmaceutical or veterinary composition which is manufactured by the use of the olefinic compound of the formula I may be a conventional formulation for oral or parenteral administration, for example a tablet, a capsule, an emulsion or an aqueous or oily solution or suspension. The composition may contain conventional pharmaceutical excipients, and may be manufactured by conventional pharmaceutical techniques.

Preferred pharmaceutical or veterinary compositions of the invention are tablets and capsules containing from 1 to 100, preferably 5 to 50 mg. of a compound of the invention.

Many of the olefinic compounds of the formula I are novel compounds, and these form a further feature of this invention. Thus, according to a further feature of the invention, there is provided an olefinic compound of the formula $R^1R^2R^3C$—$CR^4$=$CR^5R^6$ (I) wherein $R^1$ is a heterocyclyl radical selected from 1,2,4-triazolyl, imidazolyl, 5-(1–6C alkyl)imidazol-1-yl, pyridyl and pyrimidinyl; $R^2$ and $R^3$, which may be the same or different, are each a hydrogen atom or a 1–6C alkyl radical; $R^4$ is a phenyl or pyridyl radical, optionally bearing one or more substituents selected from halogen atoms, amino, cyano, carbamoyl and nitro radicals, 1–6C alkyl, halogenoalkyl, alkoxy, halogenoalkoxy, alkylamino and alkylcarbamoyl radicals, di(1–6C alkyl)amino, di(1–6C alkyl)carbamoyl and 2–6C alkoxycarbonyl radicals; $R^5$ is a hydrogen or halogen atom, a 1–6C alkyl radical or a phenyl radical optionally bearing one or more substituents as defined above for $R^4$; and $R^6$ is a phenyl or pyridyl radical optionally bearing one or more substituents as defined above for $R^4$; and for those compounds which contain a basic nitrogen atom, the pharmaceutically or veterinarily acceptable salts; but excluding those compounds wherein $R^1$ is a 1,2,4-triazol-1-yl radical, $R^2$ and $R^5$ are hydrogen, $R^3$ is methyl, $R^4$ is phenyl, 4-chlorophenyl or 2,4- or 3,4-dichlorophenyl and $R^6$ is phenyl, 4-bromophenyl or 4-tolyl, those compounds wherein $R^1$ is 1,2,4-triazol-1-yl, $R^2$, $R^3$ and $R^5$ are hydrogen, $R^4$ is phenyl, 4-chlorophenyl, 4-bromophenyl or 2,4- or 3,4-dichlorophenyl, and $R^6$ is phenyl, 4-chlorophenyl, 4-bromophenyl, 2,4-or 2,5-dichlorophenyl, 2- or 4-methoxyphenyl or 4-tolyl, and those compounds wherein $R^1$ is 1-imidazolyl, $R^2$, $R^3$ and $R^5$ are hydrogen, $R^4$ is phenyl, 4-chlorophenyl, 4-bromophenyl, 2-4-dichlorophenyl, 4-methoxyphenyl or 4-tolyl, and $R^6$ is phenyl, 4-chlorophenyl, 4-bromophenyl, or 2,3-, 2,4-or 3,4-dichlorophenyl.

Suitable values for $R^1$, $R^2$, $R^3$, $R^4$, $R^5$, $R^6$ and pharmaceutically or veterinarily acceptable salts are those given above. The novel compounds of the formula I may be in the E or Z form, or a mixture of the E and Z forms, and may be racemic or optically active, as described above.

Preferred groups of novel compounds of the invention, and particular preferred novel compounds of the invention are those defined above as preferred groups and compounds for use in the manufacture of a pharmaceutical or veterinary composition.

The novel olefinic compounds of the formula I, as defined above, may be manufactured by processes known in themselves for the manufacture of chemically analogous compounds. Thus the following processes are provided as a further feature of the invention, wherein $R^1$, $R^2$, $R^3$, $R^4$, $R^5$ and $R^6$ have the meanings defined above, unless otherwise stated:

(a) the reaction of a ketone of the formula $R^1R^2R^3C.CO.R^4$ or $R^5.CO.R^6$ with a Wittig reagent of the formula $R^5R^6CHQ$ or $R^1R^2R^3C.CHR^4Q$ respectively, wherein Q is a triphenylphosphine halide $(Hal-.Ph_3P+-)$ or dialkylphosphono $[(R^7O)_2PO-]$ radical, wherein $R^7$ is a 1–6C lower alkyl radical, which Wittig reagent may be preformed, or formed in situ;

(b) the dehydration of a hydroxy compound of the formula $R^1R^2R^3C.CR^4(OH).CHR^5R^6$; or (c) the reaction of a compound of the formula $XCR^2R^3.CR^4$=$CR^5R^6$ with a heterocyclic compound of the formula $R^1H$, or with an alkali method salt thereof, wherein X is a leaving group.

Process (a) is preferably carried out in the presence of a base, for example sodium hydride, or an alkali metal carbonate or lower alkoxide. In process (a), the ketone starting materials may be obtained in conventional manner, for example by brominating the corresponding ketone, $R^4COCR^2R^3H$, and then reacting the α-bromo ketone so obtained with an appropriate heterocyclic compound $R^1H$, or a suitable derivative thereof, for example an alkali metal salt. The Wittig reagent starting materials may also be obtained in conventional manner by reacting an appropriate bromo compound R⁵R⁶CHBr or R¹R²R³C.CHBrR⁴ with triphenylphosphine, or with potassium diethyl phosphite.

In process (b), the hydroxy compound used as the starting material may be obtained by conventional means, for example by reacting a ketone of the formula R¹R²R³C.CO.R⁴ with a Grignard reagent of the formula R⁵R⁶CH.MgBr, and the dehydration process may be carried out by conventional means such as with thionyl chloride, phosphorus oxychloride or toluene-p-sulphonic acid in toluene.

In process (c), a suitable leaving group X is, for example, a methylsulphinyl, toluene-p-sulphonyl or bromo group.

A suitable starting material of the formula XCR²R³,CR⁴=CR⁵R⁶ wherein X is a methylsulphinyl radical may be obtained by reacting a ketone R²R³CH.COR⁴ with a Wittig reagent Q.CHR⁵R⁶ to form an olefin of the formula R²R³CH.CR⁴=CR⁵R⁶. The olefin is reacted with selenium dioxide in acetic anhydride/acetic acid to form the acetoxy derivative CH₃CO.OCR²R³.CR⁴=CR⁵R⁶, and the acetoxy derivative is then hydrolysed and reacted with methylsulphinyl chloride to produce the required methylsulphinyl starting material.

As indicated above, the compounds of the invention are useful as aromatase inhibitors. Aromatase inhibition may be demonstrated by the following tests:

DEMONSTRATION OF ACTIVITY IN VITRO

Aromatase inhibitory activity was measured using the enzyme present in the microsomal fraction of human term placenta, as described by Ryan, J. Biol. Chem. 234,268,1959. Enzyme activity was determined by measuring the amount of tritiated water released from 0.5 micromolar (1B,2B-³H)testosterone after 20 minutes incubation at 37°. The method used was essentially that described by Thomson and Siiteri, J. Biol. Chem. 249,5364,1974 except that testosterone was used in place of androstenedione. Test compounds were dissolved in dimethylsulphoxide (DMSO) to achieve final concentrations of 2, 0.2 or 0.02 μg/ml. The reaction was started by the addition of 50μl of microsome suspension to 50μl of a solution containing substrate (testosterone) and cofactors (NADPH glucose-6-phosphate and glucose-6-phosphate dehydrogenase) and either DMSO alone or a DMSO solution of test compound. Each concentration of test compound was tested in triplicate. The reaction was stopped by the addition of 200μl of a 5% (w/v) suspension of charcoal in 0.5% (w/v) solution of Dextran T70 in water. After 1 hour the charcoal was precipitated by centrifugation and 150μl of supernatant removed and the amount of tritiated water present determined using a liquid scintillation counter. The number of counts in supernatant from incubations containing test compound expressed as a percentage of the counts in supernatant from incubations containing only DMSO was taken as the degree of enzyme inhibition achieved by the test compound.

DEMONSTRATION OF ACTIVITY IN VIVO

Activity in vivo was demonstrated in terms of ovulation inhibition in female rats. Daily vaginal smears were taken from rats housed under controlled lighting (lights on 06.00 hr to 20.00 hr) and those having a vaginal smear pattern consistent with 4-day ovarian cycles were selected. To these rats a single dose of test compound was given either at 16.00 hr on Day 2 of the cycle or at 12.00 hr on Day 3 of the cycle. The rats were then killed in the morning following Day 4 of the cycle—approximately 64 hours after Day 2 treatments or approximately 46 hours after Day 3 treatments—and the presence or absence of eggs in the fallopian tubes determined. The presence of eggs indicates that the rats have ovulated.

Without treatment more than 95% of rats with 4-day ovarian cycles are found to have ovulated at the time of the post-mortem examination. At an effective dose, aromatase inhibitors prevent ovulation i.e. no eggs are found in the fallopian tubes.

In the above tests, the compounds of the formula I are active at 0.5μg/ml (in vitro) and 20 mg/kg (in vivo), and the preferred compounds of the formula I are active at 0.005μg/ml (in vitro) and 0.02 mg/kg (in vivo).

The compounds of the invention also possess antifungal properties which are useful in combatting a wide variety of plant fungal diseases.

The compounds can move acropetally when applied to the plant tissue, and can also be volatile enough to be active in the vapour phase against fungi on the plant.

The compounds may be used as such for plant fungicidal purposes but are more conveniently formulated into compositions for such usage. The invention thus provides also a plant fungicidal composition comprising a compound of general formula II and a non-pharmaceutical carrier or diluent.

The invention also provides a method of combatting fungal diseases in a plant, which method comprises applying to the plant, to seed of the plant or to the locus of the plant or seed a compound of the formula II.

The compound can be applied in a number of ways, for example it can be applied, formulated or unformulated, directly to the foliage of a plant, to seeds or to the medium in which plants are growing or are to be planted, or it can be sprayed on, dusted on or applied as a cream or paste formulation, or it can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged, and the choice of a suitable conventional composition, and the method by which such a composition may be manufactured, are apparent to those skilled in the art.

The plant fungicidal compositions of this invention can comprise also other compound(s) having biological activity, e.g. compounds having similar or complementary fungicidal activity or compounds having plant growth regulating, herbicidal or insecticidal activity.

The invention is illustrated but not limited by the following Examples. Temperatures given are in degrees Celsius:

EXAMPLES 1 and 2

A suspension of 2,4-dichloro-α-(1,2,4-triazol-1-yl)acetophenone (0.64 g.), 4-methoxybenzyl-triphenylphosphonium bromide (1.16 g.), and potassium t-butoxide (0.28 g.) in toluene (50 ml.) was heated at 80°–90° for 6 hours. Water was then added and the organic layer was separated. The aqueous layer was extracted twice with toluene and the combined organic extracts were washed with water, dried over magnesium sulphate and evaporated to dryness. The resultant brown oil (1.53 g.), a mixture of E and Z isomers and triphenylphosphine oxide, was separated by medium pressure chromatography on silica, using a mixture of ethyl acetate/hexane (60:40 v/v) as eluent, into a more polar and a less polar fraction. Each of these colourless oils, which did not crystallise, was converted into a solid nitrate salt by dissolution in ethanol and treatment with a few drops of concentrated nitric acid. The resulting yellow solution was diluted with water to turbidity, and stirred at room temperature until crystallisation was complete. The white solid was removed by filtration and washed with diethyl ether to give the less polar (Z) isomer with melting point 140°–141°. (Example 1) and the more polar (E) isomer with melting point 139°–140°. (Example 2) of 2-(2,4-dichlorophenyl)-1-(4-methoxyphenyl)-3-(1,2,4-triazol-1-yl-) prop-1-ene nitrate.

EXAMPLE 3

The process described in Example 1 was repeated, using the appropriate acetophenone starting material, to give 2-(2,4-difluorophenyl)-1-(4-methoxyphenyl)-3-(1,2,4-triazol-1-yl)prop-1-ene nitrate m.p. 157°–158°.

EXAMPLES 4 and 5

A suspension of 2-[2-(1,2,4-triazol-1-yl)propionyl]-5-trifluoromethylpyridine (1.35 g.), 4-trifluoromethylbenzyltriphenylphosphonium bromide (2.32 g.) and potassium t-butoxide (0.56 g.) in toluene (65 ml.) was heated at 90° for 16 hours. The reaction mixture was poured into water and the organic layer was separated. The aqueous layer was extracted with ethyl acetate (2×100 ml.) and the combined organic layers were washed with 5N hydrochloric acid (3×50 ml.). The acid extract was basified with concentrated sodium hydroxide and extracted with diethyl ether. The extracts were washed with water, dried over magnesium sulphate and concentrated to dryness to give an oil which would not crystallise. It was therefore dissolved in ethanol and a few drops of concentrated nitric acid were added. The resulting yellow solution was diluted with water and on standing a yellow solid prepicitated. This was removed by filtration, washed with diethyl ether and dried to give 2-(5-trifluoromethylpyrid-2-yl)-3-(1,2,4-trizol-1-yl)-1-(4-trifluoromethylphenyl)but-1-ene nitrate m.p. 149°–150°. (Example 4).

By an analogous procedure, using the 4-methoxybenzyl Wittig reagent, there was obtained 1-(4-methoxyphenyl)-2-(5-trifluoromethylpyrid-2-yl)-3-(1,2,4-triazol-1-yl)but-1-ene nitrate, m.p. 120°–122°. (Example 5).

The 2-[α-(1,2,4-triazolyl)propionyl]-5-trifluoromethylpyridine used as starting material in the above Examples was prepared as follows:

To a solution of ethyl magnesium iodide [formed from ethyl iodide (46.8 g.) and magnesium turnings (7.2 g.) in anhydrous ether (250 ml.)], cooled to 0°–5°, was added a solution of 2-cyano-5-trifluoro-methylphridine (10.32 g.) in anhydrous ether (50 ml.) during 20 minutes. The resulting grey suspension was stirred at 5° for 30 minutes then poured into a mixture of ice/water/2N hydrochloric acid. After stirring for 15 minutes the mixture was extracted with ether. The organic extract was washed with water, dried over magnesium sulphate and concentrated to dryness under reduced pressure. The residue was purified on a silica column using hexane:ether (9:1 v/v) as eluent, to give 2-propionyl-5-trifluoromethylpyridine as a colourless oil.

Bromine (0.52 ml.) in chloroform (50 ml.) was added to solution of 2-propionyl 5-trifluoromethylpyridine (2.03 g.) in chloroform (20 ml.) over 1 hour under photoflood illumination. After addition was complete the reaction was stirred for 16 hours at room temperature. The reaction was then poured into water, and the organic phase was separated, washed with water, dried over magnesium sulphate and concentrated to dryness to give 2-(2-bromopropionyl)-5-trifluoromethylpyridine as an oil which was used without further purification.

To a solution of 2-(2-bromopropionyl)-5-trifluoromethylpyridine (5.8 g.) in acetonitrile (65 ml.) was added sodium 1,2,4- triazole (2.0 g.) and the solution was stirred for 90 minutes. The acetonitrile was evaporated under reduced pressure and the residue was partitioned between ethyl acetate and water. The organic layer was separated and the aqueous layer was extracted with ethyl acetate. The combined organic layer was washed with water, dried over magnesium sulphate and concentrated to dryness under reduced pressure to give a yellow gum. Chromatography on silica, using petroleum ether (bp (60°–80°):ethyl acetate 60/40 v/v as eluent, gave 2-[2-(1,2,4-triazol-1-yl)propionyl]-5-trifluoromethylpyridine as a pale yellow oil. Nmr in deuteriochloroform: δ1.88 (3H,d); 6.62 (1H,q); 7.9 (1H,s); 8.14 (2H,m); 8.36 (1H,s); 8.94 (1H,d).

EXAMPLES 6 and 7

A suspension of 4-fluoro-α-(imidazol-1-yl)acetophenone (1.0 g), (4-fluorobenzyl)triphenylphosphonium chloride (3.85 g), potassium tert-butoxide (1.1 g) and 18-crown-6 (1,4,7,10,13,16-hexaoxacyclooctadecane, 0.1g) in dichloromethane (150 ml) was stirred at room temperature for 1 h. Saturated ammonium chloride (100 ml) was then added, and the organic layer was separated. The aqueous layer was extracted twice with dichloromethane and the combined organic extracts were dried over sodium sulphate and evaporated to dryness. The resultant brown oil, a mixture of E and Z isomers and triphenylphosphine oxide, was separated by flash column chromatography on silica, using ethyl acetate and then ethyl acetate/methanol (95:5 v/v) as eluent, into a more and less polar fraction.

The less polar fraction, a colourless oil which did not crystallise, was converted into a solid hydrochloride salt by dissolution in ether and treatment with 2 ml of a solution of ethereal hydrogen chloride. The resulting white solid was filtered off and washed with diethyl ether, to give the Z-isomer of 1,2-bis(4-fluorophenyl)-3-(1-imidazolyl)prop-1-ene hydrochloride, m.p. 203° C. (Example 6). The more polar fraction was triturated with diethyl ether to give the E-isomer of the same compound, m.p. 121° C. (Example 7).

EXAMPLES 8-49

The process described for Examples 6 and 7 was repeated, using the appropriate substituted acetophenone and the appropriate (substituted benzyl)triphenylphosphonium chloride, to give the following compounds:

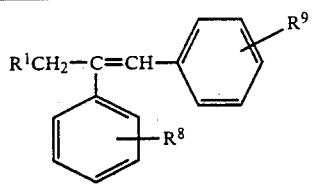

| Example | R¹ | R⁸ | R⁹ | Salt | E or Z | Mp. |
|---|---|---|---|---|---|---|
| 8 | T* | 4-Cl | 4-F | HNO₃ | E | 149–151 |
| 9 | T | 4-Cl | 4-F | — | Z | 104–105 |
| 10 | T | 4-Cl | 4-CF₂H.CF₂.CH₂O | HNO₃ | E | 132–134 |
| 11 | T | 4-Cl | 4-CF₂H.CF₂.CH₂O | — | Z | 101–103 |
| 12 | T | 4-F | 4-F | HNO₃ | E | 160–163 |
| 13 | T | 4-F | 4-F | HNO₃ | Z | 117–130 |
| 14 | T | 4-F | 4-Cl | — | E | 104–106 |
| 15 | T | 4-F | 4-Cl | — | Z | 90–93 |
| 16 | T | 4-F | 4-CF₃ | HNO₃ | E | 163–166 |
| 17 | T | 4-F | 4-CF₃ | HNO₃ | Z | 143–149 |
| 18 | T | 4-F | 4-CF₂H.CF₂.CH₂O | HNO₃ | E | 169–170 |
| 19 | T | 4-F | 4-CF₂H.CF₂.CH₂O | HNO₃ | Z | 107–111 |
| 20 | T | 4-F | 4-CN | HCl | E | 180 |
| 21 | T | 4-F | 4-CN | HCl | Z | 155 |
| 22 | T | 2,4-F₂ | 4-Cl | HNO₃ | E | 163–164 |
| 23 | T | 2,4-F₂ | 4-Cl | — | Z | 99–102 |
| 24 | T | 2,4-F₂ | 4-F | HNO₃ | E | 147–148 |
| 25 | T | 2,4-F₂ | 4-F | HNO₃ | Z | 128–130 |
| 26 | T | 2,4-F₂ | 4-CN | HCl | E | 148–149 |
| 27 | T | 2,4-F₂ | 4-CN | HCl | Z | 109 |
| 28 | T | 2,4-F₂ | 4-CH₃O | HCl | E | 148–149 |
| 29 | T | 4-CF₃ | 4-Cl | HCl | E | 156 |
| 30 | T | 4-CF₃ | 4-Cl | — | Z | 110–113 |
| 31 | T | 4-CF₃ | 4-F | HNO₃ | E | 144–147 |
| 32 | T | 4-CF₃ | 4-F | — | Z | 108–110 |
| 33 | T | 4-CN | 4-F | HCl | E | 178–180 |
| 34 | T | 4-CN | 4-F | — | Z | 148 |
| 35 | T | 4-CN | 4-CN | — | E | 129 |
| 36 | T | 4-CN | 4-CN | — | Z | 184–186 |
| 37 | I* | 4-F | 4-Cl | — | E | 132 |
| 38 | I | 4-F | 4-Cl | HCl | Z | 248 |
| 39 | I | 4-Cl | 4-F | — | E | 79 |
| 40 | I | 4-Cl | 4-F | HCl | Z | 212 |
| 41 | I | 2,4-F₂ | 4-F | — | E | 99 |
| 42 | I | 2,4-F₂ | 4-CN | — | E | 129 |
| 43 | I | 2,4-F₂ | 4-Cl | — | E | 133 |
| 44 | I | 2,4-F₂ | 4-Cl | — | Z | 163 |
| 45 | I | 4-CN | 4-F | HCl | E | 210–212 |
| 46 | I | 4-CN | 4-F | HCl | Z | 199–200 |
| 47 | I | 4-CN | 4-CN | HCl | E | 198–200 |
| 48 | I | 4-CN | 4-CN | HCl | Z | 169–170 |
| 49 | I | 4-F | 4-CN | — | Z | 104 |

*T = 1H-1,2,4-triazol-1-yl; I = 1H-imidazol-1-yl.

EXAMPLES 50-56

The process described for Examples 8-49 was repeated, using the appropriate (4-pyridylmethyl)triphenylphosphonium chloride and the appropriately α-substituted acetophenone, to give the following compounds:

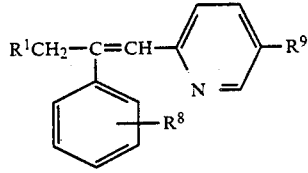

| Example | R¹ | R⁸ | R⁹ | E or Z | Mp. |
|---|---|---|---|---|---|
| 50 | T | 4-F | H | E | 129 |
| 51 | I | 4-F | H | E | 137 |
| 52 | T | 4-CN | H | Z | 190 |

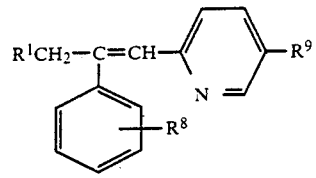

| Example | R¹ | R⁸ | R⁹ | E or Z | Mp. |
|---|---|---|---|---|---|
| 53 | T | 4-CN | 4-CN | Z | 211 |
| 54 | T | 4-CN | H | E | 129 |
| 55 | I | 4-CN | H | Z | 157 |
| 56 | I | 4-CN | H | E | 126 |

The triphenylphosphonium bromide starting material required for Example 53 was prepared as follows:

A mixture of 6-methylnicotinonitrile (4.15 g) and 3-chloroperbenzoic acid (8.3 g) in dichloromethane (200 ml) was stirred under an argon atomsphere at room temperature for 16h. The dichloromethane was evaporated under reduced pressure and the residue purified by flash column chromatography on silica (K60), using ethyl acetate and then methanol: dichloromethane (1:9 by volume) as eluting solvent to give 5-cyano-2-methylpyridine-1-oxide, mp 133.5°.

A solution of phosphoryl chloride (6.5 g) in dichloromethane (20 ml) was added to a mixture of the above pyridine-1-oxide (4.4 g) and triethylamine (4.3 g) in dichloromethane (60 ml). After the addition was completed the reaction mixture was gently refluxed for 15 mins, cooled and washed with water (30 ml). The organic layer was separated, dried over anhydrous sodium sulphate and evaporated to dryness. The residue was purified by flash column chromatography on silica (K60) using ethyl acetate: toluene (1:9 by volume) as eluting solvent, to give 6-chloromethylnicotinonitrile.

A mixture of this chloromethyl compound (2 g) and triphenylphosphine (4.11 g) in acetonitrile (80 ml) was stirred and heated under reflux for 24 h. The acetonitrile was avaporated under reduced pressure and ethyl acetate (200 ml) added to the residue. The solid was filtered and dried to give the required (4-cyanopyridyl)-triphenylphosphonium chloride, mp 267°.

EXAMPLES 57-71

The process described in Examples 6 and 7 was repeated, using the appropriate (substituted benzyl)triphenylphosphonium bromide and 1,2,4-triazole, to give the following compounds:

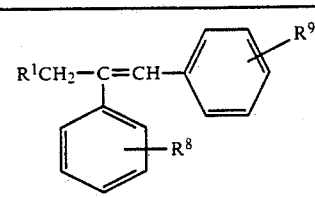

| Example | R¹ | R⁸ | R⁹ | Salt | E or Z | Mp. |
|---|---|---|---|---|---|---|
| 57 | T | 4-CN | 2,4-Cl₂ | — | Z | 122 |
| 58 | T | 4-CN | 4-Cl | — | Z | 148 |
| 59 | T | 4-CN | 2,4-F₂ | — | Z | 144–146 |
| 60 | T | 4-CN | 4-CF₃ | — | Z | 177 |
| 61 | T | 4-Cl | 4-CN | — | Z | 184 |
| 62 | T | 4-CF₃ | 4-CN | — | Z | 159 |
| 63 | T | 4-CN | 2,4-Cl₂ | HCl | E | 167 |
| 64 | T | 4-CN | 4-Cl | HCl | E | 204 |

-continued

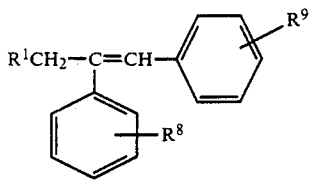

| Example | R¹ | R⁸ | R⁹ | Salt | E or Z | Mp. |
|---|---|---|---|---|---|---|
| 65 | T | 4-CN | 2,4-F₂ | — | E | 201 |
| 66 | I | 4-CN | 2,4-F₂ | HCl | Z | 214 |
| 67 | I | 4-CN | 2,4-Cl₂ | — | Z | 144 |
| 68 | I | 4-CN | 4-Cl | — | Z | 164 |
| 69 | I | 4-CN | 2,4-F₂ | — | E | 98 |
| 70 | I | 4-CN | 2,4-Cl₂ | — | E | 117 |
| 71 | I | 4-CN | 4-Cl | — | E | 106 |

EXAMPLES 72–84

The process described in Examples 6 and 7 was repeated, using an appropriately substituted α-(5-methylimidazol-1-yl)acetophenone and an appropriately substituted benzyltriphenylphosphonium salt as starting materials, to give the following compounds:

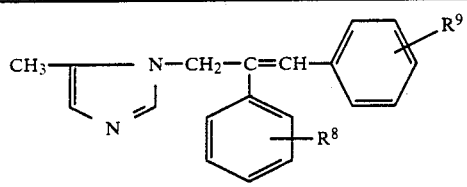

| Example | R⁸ | R⁹ | Salt | E or Z | Mp. |
|---|---|---|---|---|---|
| 72 | 4-F | 4-F | HCl | Z | 206 |
| 73 | 4-F | 4-Cl | HCl | Z | 228 |
| 74 | 4-F | 4-CN | HCl | Z | 234 |
| 75 | 4-CN | 4-CN | — | Z | 132 |
| 76 | 4-CN | 4-Cl | HCl | Z | 254 |
| 77 | 4-CN | 2,4-Cl₂ | HCl | Z | 245 |
| 78 | 4-CN | 2,4-F₂ | HCl | Z | 254 |
| 79 | 4-CN | 4-F | HCl | Z | 242 |
| 80 | 4-CN | 4-CF₃ | HCl | Z | 249 |
| 81 | 4-CN | 4-CN | HCl | E | 177 |
| 82 | 4-F | 4-F | HCl | E | 244 |
| 83 | 4-F | 4-Cl | HCl | E | 237 |
| 84 | 4-F | 4-CN | HCl | E | 229 |

The 4-fluoro-α-(5-methylmidazol-1-yl)acetophenone, used as starting material for Examples 72–74 and 82–84, was obtained as follows:

A solution of α-chloro-4-fluoroacetophenone (1 g) and 4-methyl-1-tritylimidazole (1.88 g) in acetonitrile (10 ml) was stirred and heated under reflux for 24h. The solution was cooled and the acetonitrile was evaporated under reduced pressure. Ethyl acetate (30 ml) was added to the residue and the resulting solid was filtered, washed with more ethyl acetate (30 ml) and dried. It was then dissolved in acetic acid/water (9:1 by volume) and the resulting solution was heated under reflux for 16h. The acetic acid and water were evaporated under reduced pressure, and the residue was dissolved in a mixture of saturated sodium bicarbonate solution (50 ml) and ethyl acetate (100 ml). The organic layer was separated, and the aqueous layer was extracted twice with ethyl acetate (50 ml). The combined ethyl acetate extracts were dried and evaporated to dryness, and the residue was purified by flash column chromatography on silica (K60), using methanol: dichloromethane (5:95 by volume), as the eluting solvent, to give the required 4-fluoro-α-(5-methylimidazol-1-yl)acetophenone, mp 84.5°.

The 4-cyano-α-(5-methylimidazol-1-yl)acetophenone used as starting material was prepared similarly from α-chloro-4-cyanoacetophenone.

EXAMPLES 85–86

The process described in Examples 6 and 7 was repeated using the appropriately substituted α-(1,2,4-triazol-1-yl)propiophenone as starting material, to give 1-(4-chlorophenyl)-2-(4-fluorophenyl)-3-(1,2,4-triazol-1-yl)but-1-ene nitrate, mp 147°–140° (Example 85); and 4-[2-(4-fluorophenyl)-3-(1,2,4-triazol-1-yl)but-1-enyl]-benzonitrile, mp 118°.

EXAMPLES 87–89

The process described in Examples 6 and 7 was repeated, using the appropriately-substituted α-methylbenzyl)- or α-fluorobenzyl)triphenylphosphonium salt as starting material, to give the following compounds:

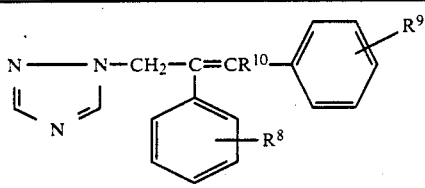

| Example | R⁸ | R⁹ | R¹⁰ | E or Z | Mp. |
|---|---|---|---|---|---|
| 87 | 4-F | 4-Cl | CH₃ | Z | 76 |
| 88 | 4-CN | 4-CN | F | Z | (a) |
| 89 | 4-CN | 4-CN | F | E | (b) |

Footnotes:
(a) NMR in deuteriochloroform: δ 8.1 (1H,s); 7.9(1H,s); 7.65(2H,d); 7.5(2H,d); 7.3(2H,d); 7.25(2H,d); 5.35(2H,d).
(b) NMR in deuteriochloroform: δ 8.25(1H,s); 8.05(1H,s); 8.05(2H,d); 7.85(2H,d); 7.65(2H,d); 7.4(2H,d); 5.2(2H,s).

The (4-cyano-α-fluorobenzyl)triphenylphosphonium bromide used as the starting material for Examples 88 and 89 was obtained as follows:

A mixture of 4-(bromomethyl)benzonitrile (1 g), potassium fluoride 20% by weight on calcium fluoride (3 g) and 18-crown-6 (0.1 g) in acetonitrile (75 ml) was stirred and heated under reflux for 3 days. The acetonitrile was evaporated under reduced pressure, and ether (50 ml) added to the residue. The solid was filtered and washed twice with ether (100 mls). The filtrate and washings were combined and the ether evaporated under reduced pressure to give 4-fluoromethyl)-benzonitrile, as a colourless oil.

A mixture of this oil (0.05 g), N-bromosuccinimide (0.8 g) and benzoyl peroxide (0.01 g) in carbon tetrachloride (25 ml), was stirred under reflux for 24 h. The mixture was cooled and the solid was filtered off. The filtrate was evaporated to dryness and the residue was purified by flash column chromatography on silica (K60) using toluene as the eluting solvent, to give 4-(bromofluoromethyl)-benzonitrile.

A mixture of this compound (0.45 g) and triphenylphosphine (0.55 g) in acetonitrile (20 ml) was stirred and heated under reflux for 48h. The acetonitrile was evaporated under reduced pressure and ethyl acetate was (20 ml) added to the residue. The solid was filtered, washed with ether (50 ml) and dried to give the required (4-cyano-α-fluorobenzyl)triphenylphosphonium bromide, mp 234.5°.

We claim:

1. A pharmaceutical or veterinary composition comprising an olefinic compound of the formula:

$$R^1R^2R^3C-CR^4=CR^5R^6 \qquad (I)$$

wherein $R^1$ is 1,2,4-triazolyl; $R^2$ and $R^3$, which may be the same or different, are each a hydrogen atom or a 1-6C alkyl radical; $R^4$ is phenyl radical, optionally bearing one or more substituents selected from halogen atoms, amino, cyano, carbamoyl and nitro radicals, 1-6C alkyl, halogenoalkyl, alkoxy, halogenoalkoxy, alkylamino and alkylcarbamoyl radicals, di(1-6C alkyl)amino, di(1-6C alkyl)carbamoyl and 2-6C alkoxycarbonyl radicals; $R^5$ is a hydrogen or halogen atom, a 1-6C alkyl radical or a phenyl radical optionally bearing one or more substituents as defined above for $R^4$; and $R^6$ is a phenyl radical optionally bearing one or more substituents as defined above for $R^4$; or, for those compounds which contain a basic nitrogen atom, the pharmaceutically or veterinarily acceptable salts thereof, together with a pharmaceutically or veterinarily acceptable diluent or carrier, but excluding a composition in the form of a non-sterile solution, emulsion, emulsifiable concentrate, suspension, powder, paste, or granule.

2. A pharmaceutical or veterinary composition in dosage unit form comprising an olefinic compound of the formula:

$$R^1R^2R^3C-CR^4=CR^5R^6 \qquad (I)$$

wherein $R^1$ is 1,2,4-triazolyl; $R^2$ and $R^3$, which may be the same or different, are each a hydrogen atom or a 1-6C alkyl radical; $R^4$ is a phenyl radical, optionally bearing one or more substituents selected from halogen atoms, amino, cyano, carbamoyl and nitro radicals, 1-6C alkyl, halogenoalkyl, alkoxy, halogenoalkoxy, alkylamino and alkylcarbamoyl radicals, di(1-6C alkyl)amino, di(1-6C alkyl)carbamoyl and 2-6C alkoxycarbonyl radicals, $R^5$ is a hydrogen or halogen atom, a 1-6C alkyl radical or phenyl radical optionally bearing one or more substituents as defined above for $R^4$; and $R^6$ is a phenyl radical optionally bearing one or more substituents as defined above for $R^4$; or, for those compounds which contain a basic nitrogen atom, the pharmaceutically or veterinarily acceptable salts thereof, together with a pharmaceutically or veterinarily acceptable diluent or carrier.

* * * * *